(12) United States Patent
Nemirovsky

(10) Patent No.: US 11,585,773 B2
(45) Date of Patent: Feb. 21, 2023

(54) GAS SENSING DEVICE AND A METHOD FOR SENSING GAS

(71) Applicants: TODOS TECHNOLOGIES LTD., AirPort City (IL); TECHNION RESEARCH AND DEVELOPEMENT FOUNDATION LTD., Haifa (IL)

(72) Inventor: Yael Nemirovsky, Haifa (IL)

(73) Assignees: TODOS TECHNOLOGIES LTD., Airport City (IL); TECHNION RESEARCH AND DEVELOPEMENT FOUNDATION LTD, Haifa (IL)

( * ) Notice: Subject to any disclaimer, the term of this patent is extended or adjusted under 35 U.S.C. 154(b) by 149 days.

(21) Appl. No.: 16/580,120

(22) Filed: Sep. 24, 2019

(65) Prior Publication Data
US 2020/0088664 A1 Mar. 19, 2020

Related U.S. Application Data

(63) Continuation of application No. 15/312,655, filed as application No. PCT/IL2015/050533 on May 19, 2015, now abandoned.
(Continued)

(51) Int. Cl.
*G01N 27/16* (2006.01)
*G01N 25/20* (2006.01)
(Continued)

(52) U.S. Cl.
CPC ............. *G01N 27/16* (2013.01); *G01K 7/01* (2013.01); *G01K 7/015* (2013.01); *G01N 25/20* (2013.01);
(Continued)

(58) Field of Classification Search
None
See application file for complete search history.

(56) References Cited

U.S. PATENT DOCUMENTS 5,345,213 A * 9/1994 Semancik ................ B01L 7/54
257/253
6,071,476 A * 6/2000 Young .................... G01N 25/30
422/51
(Continued)

FOREIGN PATENT DOCUMENTS

DE 3519397 A1 * 12/1986 ........... G01N 27/185
DE 4442396 A1 * 5/1996 ........... G01N 27/128
JP 3583704 B2 * 11/2004 ................ G01J 5/22

OTHER PUBLICATIONS

Article titled "Thermal Conductivity of Metals, Metallic Elements and Alloys" by The Engineering Tool Box retreived on Jul. 18, 2019 and available at https://www.engineeringtoolbox.com/thermal-conductivity-metals-d_858.html. (Year: 2019).*
(Continued)

*Primary Examiner* — Daniel J Colilla
(74) *Attorney, Agent, or Firm* — Reches Patents

(57) ABSTRACT

A gas sensing device, comprising a bulk and an array of gas sensing elements that are thermally isolated from the bulk, wherein each gas sensing element of a plurality of gas sensing elements of the array comprises (i) a gas reactive element that has a gas dependent temperature parameter; (ii) a semiconductor temperature sensing element that is thermally coupled to the gas reactive element and is configured to generate detection signals that are responsive to a temperature of the gas reactive element; and (iii) multiple heating elements that are configured to heat the gas reactive element to at least one predefined temperature.

24 Claims, 13 Drawing Sheets

Related U.S. Application Data

(60) Provisional application No. 62/001,093, filed on May 21, 2014.

(51) Int. Cl.
  *G01N 25/30*  (2006.01)
  *G01N 33/00*  (2006.01)
  *G01K 7/01*   (2006.01)
  *H01L 21/764* (2006.01)

(52) U.S. Cl.
  CPC ......... *G01N 25/30* (2013.01); *G01N 33/0031* (2013.01); *H01L 21/764* (2013.01)

(56) References Cited

U.S. PATENT DOCUMENTS

| | | | |
|---|---|---|---|
| 2005/0277288 A1* | 12/2005 | Ozguz | H01L 23/481 |
| | | | 438/637 |
| 2014/0231933 A1* | 8/2014 | Yu | H01L 29/66 |
| | | | 257/414 |
| 2015/0253265 A1* | 9/2015 | Whitten | G01N 25/4826 |
| | | | 506/9 |

OTHER PUBLICATIONS

Article titled "Thermal Conductivity of Doped Polysilicon Layers" by McConnell et al. and published on Sep. 3, 2001. (Year: 2001).*

Article titled "CMOS Temperature Sensors—Concepts, State-Of-The-Art and Prospects" by Udrea et al. and published in 2008. (Year: 2008).*

\* cited by examiner

```
┌─────────────────────────────────────────────────────────────────────────┐
│  Heating, to a predefined temperature, a gas reactive element that belongs to a gas │
│          sensing element and has a gas dependent temperature. 610        │
└─────────────────────────────────────────────────────────────────────────┘
                                      │
                                      ▼
┌─────────────────────────────────────────────────────────────────────────┐
│ Generating, by a semiconductor temperature sensing element that belongs to the gas │
│ sensing element and is thermally coupled to the gas reactive element, detection signals │
│  that are indicative of a temperature of the gas reactive element. The gas sensing │
│        element is thermally isolated from a bulk of a gas sensing device. 620 │
└─────────────────────────────────────────────────────────────────────────┘
                                      │
                                      ▼
┌─────────────────────────────────────────────────────────────────────────┐
│  Processing, by a readout circuit of the gas sensing device, the detection signals to │
│    provide information about gas that affected the temperature of the gas reactive │
│                              element. 630                                │
└─────────────────────────────────────────────────────────────────────────┘
```

600            FIG. 6

GAS SENSING DEVICE AND A METHOD FOR SENSING GAS

RELATED APPLICATIONS

This application claims priority from U.S. provisional patent Ser. No. 62/001,093 filing date May 21, 2014 which is incorporated herein by reference.

BACKGROUND OF THE INVENTION

Resistance-based gas sensing devices are inaccurate. The resistance of the gas sensing device can vary according to various parameters that are not related to the gas that is detected. For example—an adsorption of oxygen/oxidizing gases increases resistance of an n-type gas sensing device while an adsorption (on surface) of the gas that is being detected (reducing gases) decreases the resistance. Furthermore—the gas flow may affect the resistance of the gas sensing element.

There is a growing need to provide a reliable gas sensing device.

SUMMARY OF THE INVENTION

According to an embodiment of the invention there may be provided a gas sensing device, may include a bulk and an array of gas sensing elements that are thermally isolated from the bulk, wherein each gas sensing element of a plurality of gas sensing elements the array may include (i) a gas reactive element that has a gas dependent temperature parameter; and (ii) a semiconductor temperature sensing element that is thermally coupled to the gas reactive element and may be configured to generate detection signals that are responsive to a temperature of the gas reactive element.

Each gas sensing element of the plurality of gas sensing elements may include a plurality of gas reactive elements and a plurality of semiconductor temperature sensors; each semiconductor temperature sensing element is thermally coupled to a single gas reactive element and is thermally isolated from other semiconductor temperature sensors of the multiple semiconductor temperature sensors.

The gas sensing device may include at least one reference sensing element that may include a semiconductor temperature sensing element that is not thermally coupled to a gas reactive element.

The at least two gas sensing elements of the array may be configured to sense different gases.

The at least two gas sensing elements of the array differ from each other by their gas reactive elements.

The at least two gas sensing elements of the array have a same gas reactive element.

The semiconductor temperature sensing element may be configured to heat the gas reactive element to at least one predefined temperature.

Each gas sensing element of the plurality of gas sensing elements may include a heating element that may be configured to heat the gas reactive element to at least one predefined temperature.

In each gas sensing element of the plurality of gas sensing elements the heating element may surround the semiconductor temperature sensing element.

In each gas sensing element the heating element may be spaced apart from the semiconductor temperature sensing element.

In each gas sensing element of the plurality of gas sensing elements the heating element may be a polysilicon resistor that may be spaced apart from the semiconductor temperature sensing element.

The at least one predefined temperature may include multiple predefined temperatures that are associated with a sensing of multiple gases that differ from each other; wherein in each gas sensing element the heating element may be configured to heat the gas reactive element, at different points in time, to the multiple predefined temperatures.

Each heating element may be configured to heat the gas reactive element in a noncontinuous manner.

The gas sensing device may include a signals source, an interfacing module and a readout circuit; wherein the interfacing module electrically couples the array to the signals source and to the readout circuit; wherein the signals source may be configured to supply bias signals to at least one gas sensing element of the array; wherein the readout circuit may be configured to read detection signals from one or more.

Each gas sensing element of the plurality of gas sensing elements may include a heating element that may be configured to heat the gas reactive element to at least one predefined temperature; and wherein the signals source may be configured to supply bias signals to heating elements of the array.

The signals source may be configured to provide pulsed bias signals.

The signals source may be configured to provide bias current signals; and wherein the detection signals are voltage detection signals.

The signals source may be configured to provide to the gas sensing elements of the array at least one voltage bias signal; and wherein the detection signals are current detection signals.

The readout circuit may be configured to read differential detection signals.

Each gas sensing element of the plurality of gas sensing elements may be mechanically supported by at least supporting element.

Each gas sensing element of the plurality of gas sensing elements may be mechanically supported by a plurality of spaced apart supporting elements.

The bulk may be micro-machined or nano-machined to form a gap between the bulk and the array of gas sensing elements.

In each gas sensing element of the plurality of gas sensing elements the semiconductor temperature sensing element may be a Complementary Metal Oxide Semiconductor (CMOS) temperature sensor.

The array may include a plurality (N) of gas sensing elements that may be configured, at a certain point in time, to differ from each other by their response to materials; wherein the gas sensing device may be configured to detect a composition of up till N different gaseous materials by processing the detection signals from the plurality of gas sensing elements.

According to an embodiment of the invention there may be provided a method for sensing gas by a gas sensing device, the method may include: heating to a predefined temperature a gas reactive element that belongs to a gas sensing element and has a gas dependent temperature; generating, by a semiconductor temperature sensing element that belongs to the gas sensing element and is thermally coupled to the gas reactive element, detection signals that are indicative of a temperature of the gas reactive element;

wherein the gas sensing element is thermally isolated from a bulk of a gas sensing device; processing, by a readout circuit of the gas sensing device, the detection signals to provide information about gas that affected the temperature of the gas reactive element.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

FIG. 6 illustrates a method according to an embodiment of the invention;

Figure 1A:
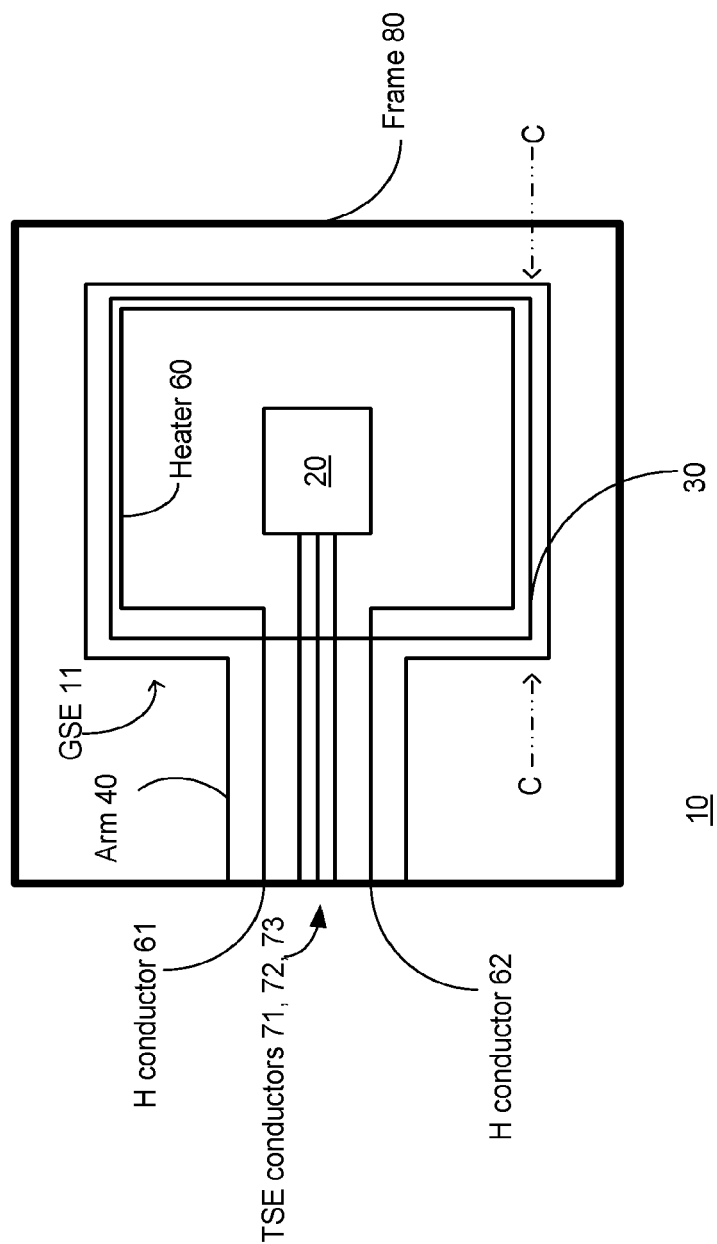
FIG. 1A illustrates a frame, an arm, a gas sensing element and various conductors according to an embodiment of the invention.

It will be appreciated that for simplicity and clarity of illustration, elements shown in the Figures have not necessarily been drawn to scale. For example, the dimensions of some of the elements may be exaggerated relative to other elements for clarity. Further, where considered appropriate, reference numerals may be repeated among the Figures to indicate corresponding or analogous elements.

DETAILED DESCRIPTION OF THE PRESENT INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings.

Because the illustrated embodiments of the present invention may for the most part, be implemented using electronic components and circuits known to those skilled in the art, details will not be explained in any greater extent than that considered necessary as illustrated above, for the understanding and appreciation of the underlying concepts of the present invention and in order not to obfuscate or distract from the teachings of the present invention.

Any reference in the specification to a method should be applied mutatis mutandis to a gas sensing device capable of executing the method.

Any reference in the specification to a gas sensing device should be applied mutatis mutandis to a method that may be executed by the gas sensing device.

FIG. 1A illustrates a frame 80, an arm 40, a gas sensing element (GSE) 11 and various conductors according to an embodiment of the invention.

Gas sensing element 11 is illustrates as including (i) a gas reactive element 30 that has a gas dependent temperature parameter; (ii) a semiconductor temperature sensing element 20 that is thermally coupled to the gas reactive element 30 and is configured to generate detection signals that are responsive to a temperature of the gas reactive element 30, and (iii) heater 60.

Heater 60 may be configured to heat the gas reactive element 30 to a predefined temperature that is suited (for that gas reactive element 30) for sensing a predefined gas. Gas reactive elements 30 made of different materials may sense different gases. Additionally or alternatively, heating a gas reactive element to different predefined temperatures will assist in detecting different gases.

The gas reactive element 30 can be made of a catalytic metal. A chemical reaction between the gas reactive element 30 and a certain gas may change the temperature of the gas reactive element 30. The semiconductor temperature sensing element 20 is thermally coupled to the gas reactive element and thus is able to sense the temperature of the gas reactive element 30. It is noted that the heating device may be omitted from the gas sensing element.

Gas sensing element 11 may be suspended—it is positioned above a bulk (not shown) and is thermally isolated from the bulk.

Arm 40 supports the gas sensing element 11 as well as supports conductors such as heater conductors 61 and 62 and semiconductor temperature sensing element (TSE) conductors 71, 72 and 73. Arm 40 is connected to or interfaces with frame 80.

The TSE conductors should be electrically conductive but have a poor thermal conduction (at least have a thermal conduction below a predefined threshold) in order to reduce and even eliminate any thermal effect that the bulk may have on the semiconductor temperature sensing element 20. The TSE conductors can be made, for example, from doped polysilicon or active silicon.

The semiconductor temperature sensing element 20 may be a transistor such as a CMOS transistor and TSE conductors 71, 72 and 73 may be electrically coupled to a source, a drain and a gate of the CMOS transistor.

It is noted that the CMOS transistor may have its gate and drain shorted and may be fed by a pair of TSE conductors.

It is noted that the semiconductor temperature sensing element 20 may differ from a CMOS transistor.

Heater 60 may be fed by heater conductors 61 and 61. Heater 60 may be fed with continuous or non-continuous signals for activating the heater 60. For example, heater 60 may be provided (via heater conductors 61 and 62) with current pulses that may heat the heater 60 to a predefined temperature.

In FIG. 1A heater 60 surrounds semiconductor temperature sensing element 20.

The heater conductors 61 and 62 may be made of Doped polysilicon, active silicon, aluminum or any other metal.

In FIG. 1A the heater 60 is positioned above the semiconductor temperature sensing element 20. It is noted that heater 60 may be positioned at the same height as the semiconductor temperature sensing element 20—and is preferably spaced apart from the semiconductor temperature sensing element 20.

Figure 2A:
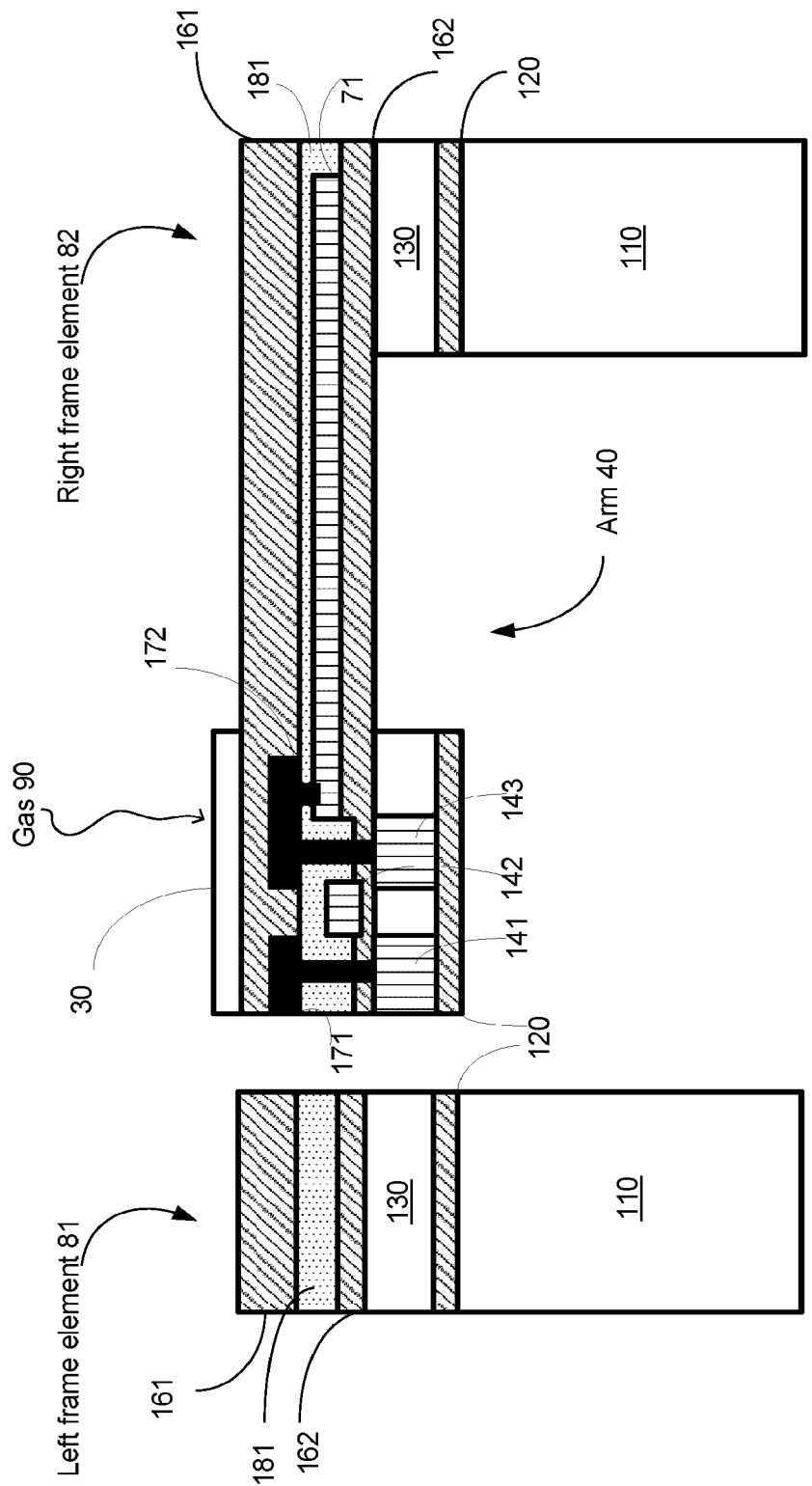
FIG. 2A is a cross sectional view of a frame, an arm and a gas sensing element according an embodiment of the invention.
Figure 2B:
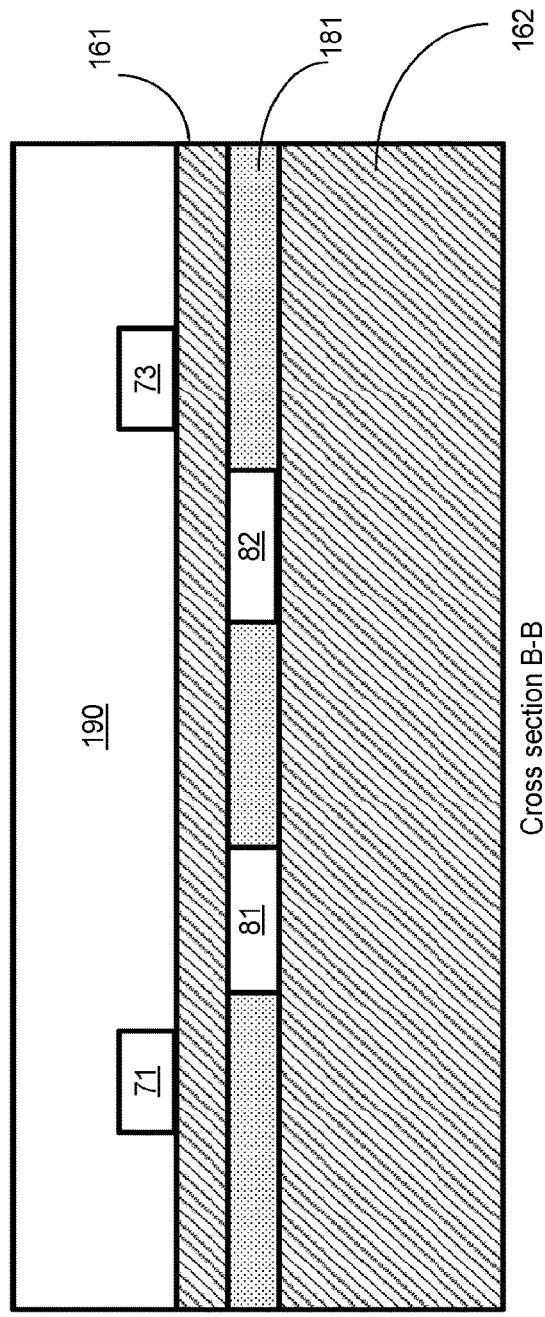
FIG. 2B illustrates a cross sections of an arm and various conductors and a cross section of a gas sensing element according to various embodiments of the invention.
Figure 2B:
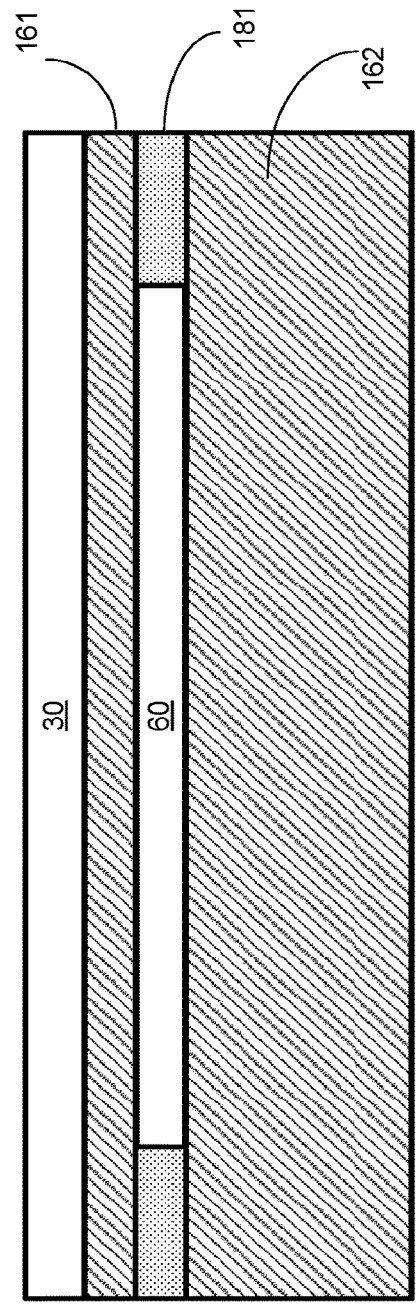

FIG. 1A illustrates an imaginary plane C-C. FIG. 2B illustrates a cross section along plane C-C.

Figure 1B:
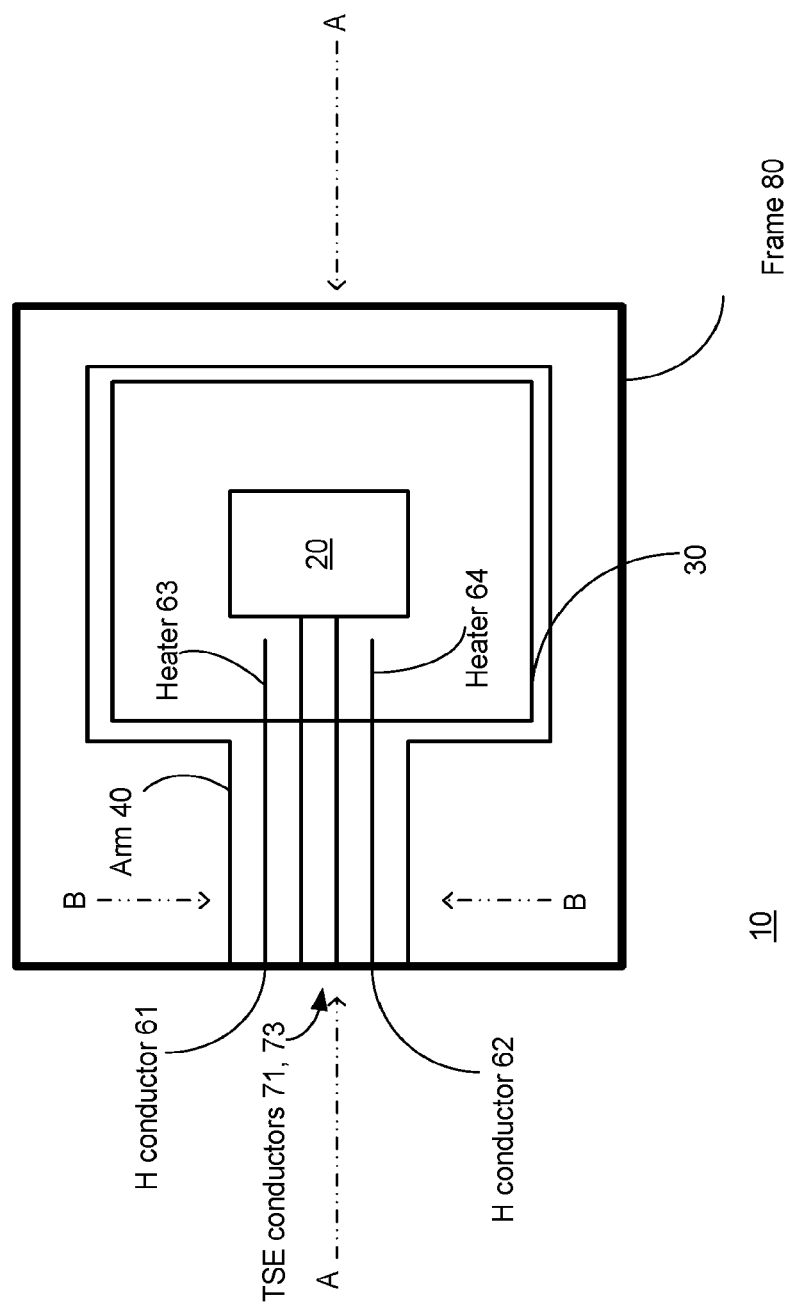
FIG. 1B illustrates a frame, an arm, a gas sensing element and various conductors according to an embodiment of the invention.

FIG. 1B illustrates frame 80, an arm 40, a gas sensing element (GSE) 11 and various conductors according to another embodiment of the invention.

In FIG. 1B there are only two TSE conductors 71 and 73 and the semiconductor temperature sensing element 20 is not surrounded by a heater—as illustrated by heater portions 63 and 64.

In FIG. 1B the semiconductor temperature sensing element 20 can be a CMOS diode or any other diode as well as a transistor that is coupled as a diode.

FIG. 1B illustrates imaginary planes A-A and B-B. FIG. 2A illustrates a cross section along plane A-A. FIG. 2B illustrates a cross section along plane B-B.

Figure 1C:
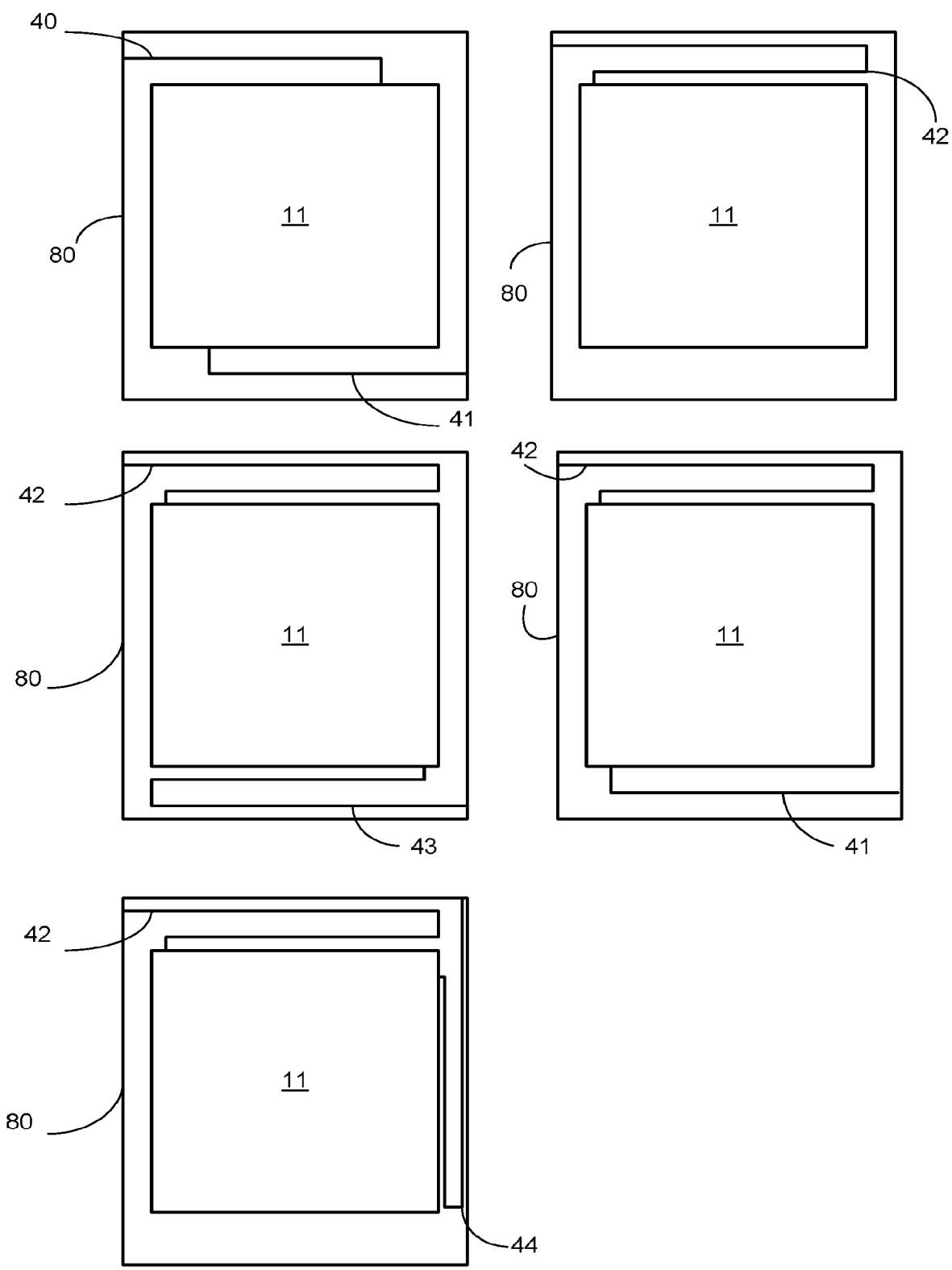
FIG. 1C illustrates a frame, various arms, and various gas sensing elements according to various embodiments of the invention.

FIG. 1C illustrates a frame 80, various arms 40, 41, 42, 43 and 44 and various gas sensing elements 11 according to various embodiments of the invention.

FIG. 1C illustrates that a gas sensing element 11 may be supported by one arm or more arms (for example two arms), and that the arms may have different shapes.

The shape and size of the arms may change. As a rule of thumb longer arms (for example arms 42, 43 and 44) provide better thermal isolation from shorter arms (for example arms 40 and 41) that are made of the same materials.

FIG. 2A is a cross sectional view (along plane A-A) of a frame, an arm and a gas sensing element according an embodiment of the invention.

Frame 80 is illustrated as has having a left frame element 81 and a right frame element 82.

FIG. 2A illustrates a semiconductor temperature sensing element such as a CMOS transistor that includes drain 141, source 143 and gate 142. Drain 141 is coupled to a drain conductor 171. Source 143 is coupled to a source conductor 172. Source conductor 171 and drain conductor 172 are made of metal and may be coupled to TSE conductors 71 and 72 respectively. The gate 142 may be coupled to a gate conductor (now shown).

Drain 141 and source 143 may be positioned above a thin silicon dioxide layer 120 that can be formed on top of thick silicon bulk 110.

Bulk 110 and device layer 130 may be micro-machined or nano-machined to form a suspended gas sensing element.

Thin silicon dioxide layer 120 of the buried oxide may serve as an etch stop layer for the bulk micromachining process and separates the bulk silicon from the thin device single crystal silicon layer 130.

The stack of thin device silicon layer 130 on top of thin silicon dioxide layer 120 on top of thick silicon bulk 110 is known as SOI and may be fabricated by several techniques, well known for the experts. An increase in the top silicon layer thickness, and increased control of its properties, is preferably achieved using epitaxial growth of silicon.

The non-etched silicon bulk 110 serves as a heat sink to the thermal sensors due to the high thermal conductivity of the silicon and the large thickness of silicon bulk 110. Silicon bulk 110 is etched under the sensor area in order to provide thermal isolation for increased temperature responsivity.

Above the etched area a structure composed of layers such as but not limited to Complementary Metal Oxide Semiconductor (CMOS) thin film layers—such as first insulating layers 161 and second insulating layer 162—both known as Inter Level Dielectrics.

FIG. 2A illustrate a TSE conductor 171 that is coupled to source conductor 172. First and second insulating layers 161 and 162 and separated by intermediate layer 181.

Non-limiting dimensions of are provided below:

| Element | Dimensions (in Angstrem) |
| --- | --- |
| Gas reactive element 30 | 100-500 (Thickness) |
| First insulating layer 161 | 4000 (Thickness) |
| Source conductor 171 (horizontal part) | 330-2600 (Thickness) |
| Buried oxide 120 | 4000-10000 (Thickness) |
| Gate oxide 142 | 20-50 (Thickness), |
| Source 141 and drain 143 | 145-150 (Thickness) |
| Polysilicon Gate | 2000 A |

FIG. 2B illustrates a cross sections of an arm and various conductors and a cross section of a gas sensing element according to various embodiments of the invention.

FIG. 2B illustrates a cross section of arm 40 taken along plane B-B.

Arm 40 includes heater conductors 61 and 62 as well as TSE conductors 72 and 73. Heater conductors 81 and 82 are formed in intermediate layer 181. TSE conductors 72 and 73 are form in a top layer 190. First insulating layer 161 is positioned between top layer 190 and intermediate layer 181. Intermediate layer 181 is supported by second insulating layer 162.

FIG. 2B also illustrates a cross section of the gas sensing element along plane C-C. This cross section includes the gas reactive element 30 on top of layer 161, on top of heater 60 and surrounding elements and on top of layer 162.

Heater 60 is formed in intermediate layer 181. Gas reactive element 30 is positioned above first insulating layer 161.

First insulating layer 161 can be made of a dielectric layer composed of oxide or nitride.

Figure 3A:
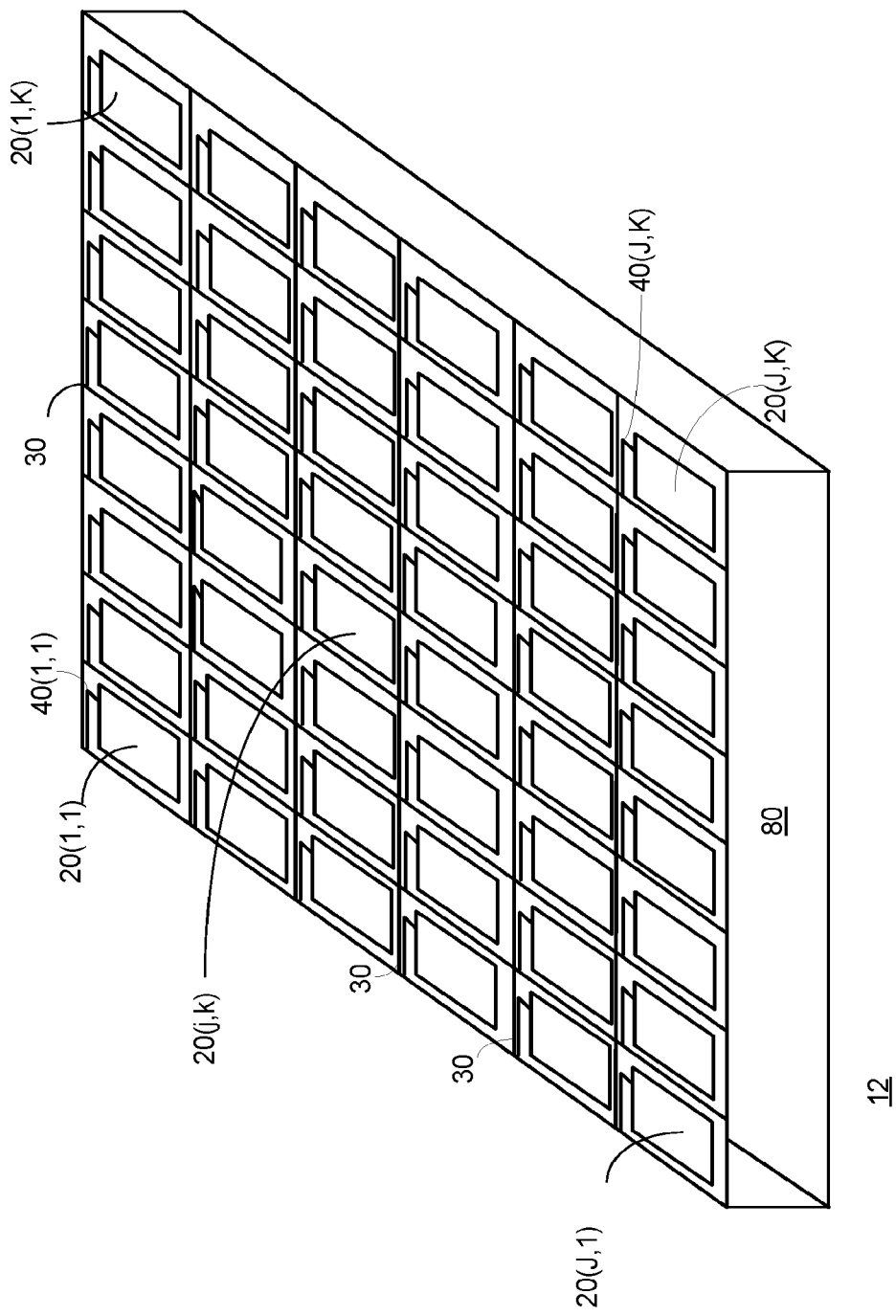
FIG. 3A illustrates frame, arms and an array of gas sensing elements according to an embodiment of the invention.

FIG. 3A illustrates an array of gas sensing elements, according to various embodiments of the invention.

FIG. 3A illustrates a rectangular array of gas sensing elements 20(1,1)-20(J,K) that include K columns and J rows of gas sensing elements. J and K are positive integers that exceed one.

Different gas sensing elements of the array may be configured to sense the same gas or different gases. A composition of the gas reactive element and, additionally or alternatively, a temperature to which the gas reactive element is heated may determine which gas is sensed by the gas reactive element.

The gas sensing elements of the array are supported by arms 40(1,1)-40(J,K) to a grid of frames collectively denoted 80.

Each gas sensing element may be connected to one or more arms.

Figure 3B:
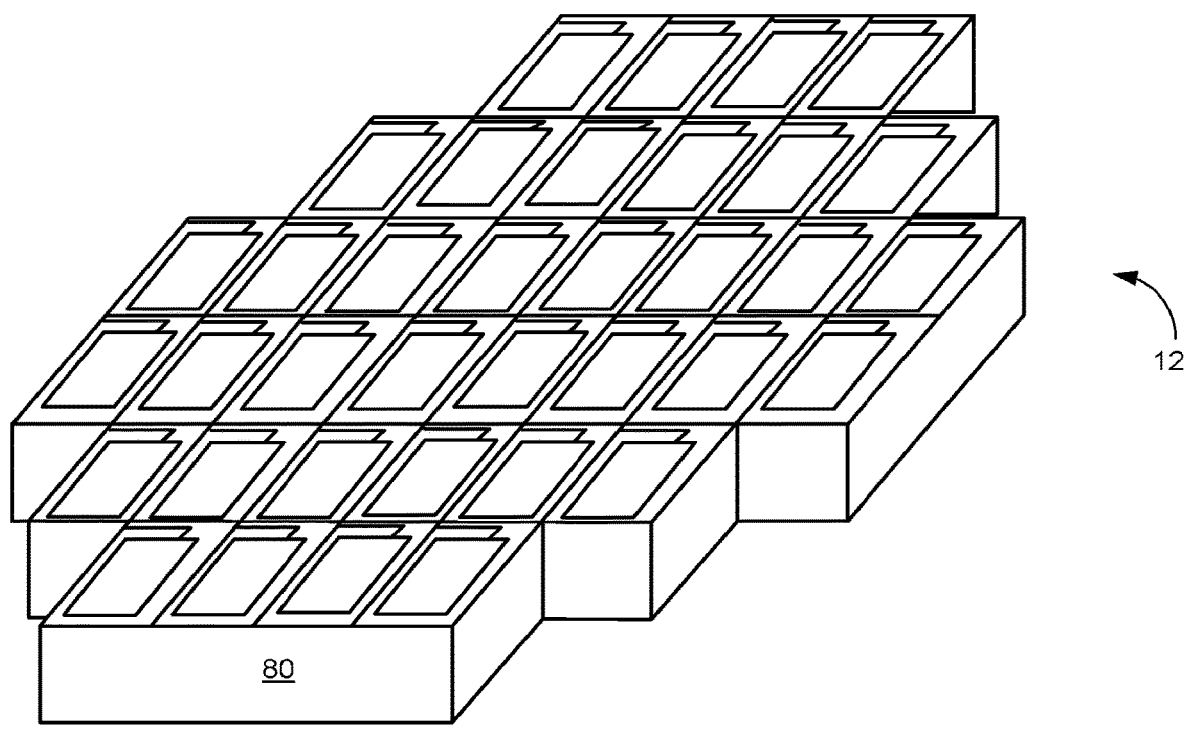
FIG. 3B illustrates frames, arms and an array of gas sensing elements according to an embodiment of the invention.

The gas sensing elements may be arranged to form other arrays. For example—a linear array, a non-rectangular array, a polygonal array, a circular array or any arrangements of multiple sensing elements. FIG. 3B illustrates a non-rectangular array of gas sensing elements.

The gas sensing elements in the array may be connected electrically in parallel or serially or in a combination of serially and parallel configurations in order to maximize the signal to noise.

Gas sensing elements that are configured to sense different materials may be used for sensing gaseous mixtures that include different materials. For example if there are N gas sensing elements and each gas sensing element is configured to sense a different material (or otherwise has a different response to materials that the other gas sensing elements) than the N gas sensing element may detect a composition of up till N different gaseous materials. When exposed to a mixture of For example, assuming four different gas sensing elements and a gaseous mixture of four different materials:

$$\begin{bmatrix} A11 & A12 & A13 & A14 \\ A21 & A22 & A23 & A24 \\ A31 & A32 & A33 & A34 \\ A41 & A42 & A43 & A44 \end{bmatrix} * \begin{bmatrix} G1 \\ G2 \\ G3 \\ G4 \end{bmatrix} = \begin{bmatrix} O1 \\ O2 \\ O3 \\ O4 \end{bmatrix} \quad (1)$$

$$\begin{bmatrix} A11 & A12 & A13 & A14 \\ A21 & A22 & A23 & A24 \\ A31 & A32 & A33 & A34 \\ A41 & A42 & A43 & A44 \end{bmatrix}^{-1} * \begin{bmatrix} O1 \\ O2 \\ O3 \\ O4 \end{bmatrix} = \begin{bmatrix} G1 \\ G2 \\ G3 \\ G4 \end{bmatrix} \quad (2)$$

Equation (1) illustrates that the detection signals of each gas sensing element are a superposition of the reactions of the gas sensing element to each one of the components of the gaseous mixture. Equation (2) is extracted from equation (1).

G1, G2, G3 and G4 are the concentrations of the first, second, third and fourth materials of the gaseous mixture. O1, O2, O3 and O4 are the detection signals of the first, second, third and fourth gas sensing elements and for indexes i and j that range between 1 and 4 Aij is the reaction coefficient of the i'th gas sensing element to the j'th material of the gaseous mixture.

Figure 4A:
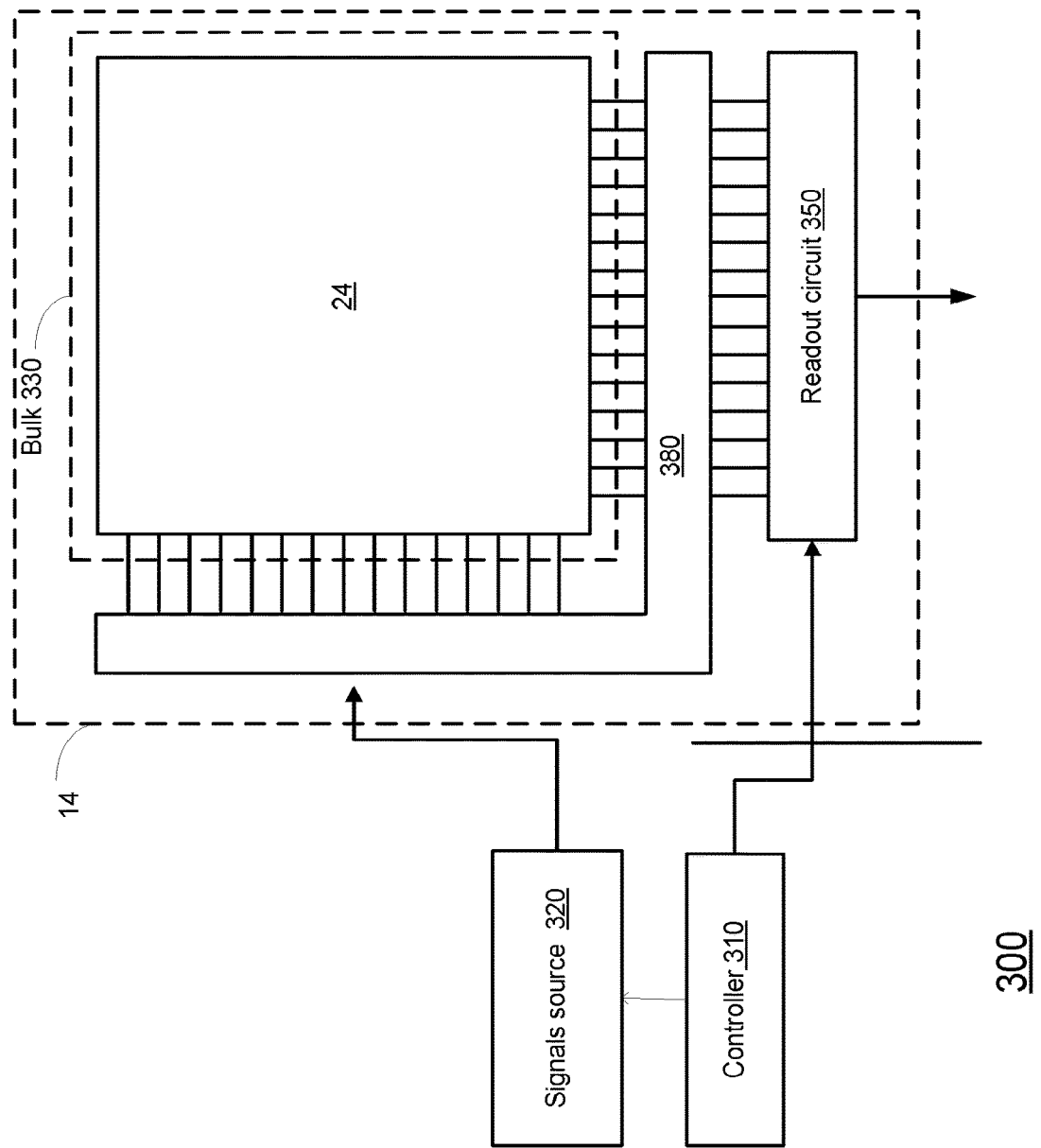
FIG. 4A illustrates a gas sensing device according to an embodiment of the invention.

FIG. 4A illustrates a gas sensing device 300 according to an embodiment of the invention.

Gas sensing device 300 includes a controller 310, signals source 320, bulk 330, interfacing module 380, readout circuit 350 and an array 24 of gas sensing elements.

Although interfacing module 380 is illustrates as a separate entity from the array 24, both array 24 and interfacing module 380 may be integrated.

Interfacing module 380 may couple between the array 24 to the signals source 320 and to the readout circuit 350.

Readout circuit 350 may read detection signals from one or more gas sensing elements at a time. For example—the readout circuit 350 may read a single row of array 24, a part of a row, more than a single row, a column, a part of a column, more than a column and even the entire array at once.

Readout circuit 350 may read current detection signals, voltage detection signals, differential detection signals and the like.

Gas sensing device 300 may include reference sensing elements. The reference sensing elements may be included in array 24 or outside array 24. A reference sensing element has a semiconductor temperature sensing element but does not include a gas reactive element. Alternatively, the semiconductor temperature sensing element is not thermally coupled to the gas relative element or otherwise is not substantially affected by gas reactions.

According to an embodiment of the invention the interfacing module 380 may also electrically couple between different gas sensing elements of the array 24. The interfacing module 380 may couple certain gas sensing elements of the array in serial to each other during one measurement and couple the certain gas sensing elements of the array in parallel to each other during another measurement. Any combination of serial and parallel couplings between gas sensing elements may be provided. The interfacing module 380 may include any combination of switches, interconnects and the like.

Signals source 310 is configured to supply bias signals to at least one gas sensing element of the array 24. The bias signals may include voltage bias signals and/or current bias signals. Some bias signals may set one or more semiconductor temperature sensing elements to one or more desired working points. Other bias signals may determine the heating applied by one or more heaters.

The bias signals may be provided in a continuous manner or in a non-continuous manner. The latter may reduce the power consumption of the gas sensing device. Conveniently, a first pulse aimed to bias a semiconductor temperature sensing elements of a certain gas sensing element is synchronized with a second pulse aimed to bias a heater of the certain gas sensing element. The second pulse may begin before the first pulse. The first and second pulse may be partially overlapping, fully overlapping or non-overlapping.

Controller 310 is configured to control the operation of the gas sensing device 300.

Controller 310, signals source 320, bulk 330, interfacing module 380, readout circuit 350 and array 24 of gas sensing elements may be formed on the same chip. The gas sensing device 300 may be fabricated using CMOS technology.

Figure 4B:
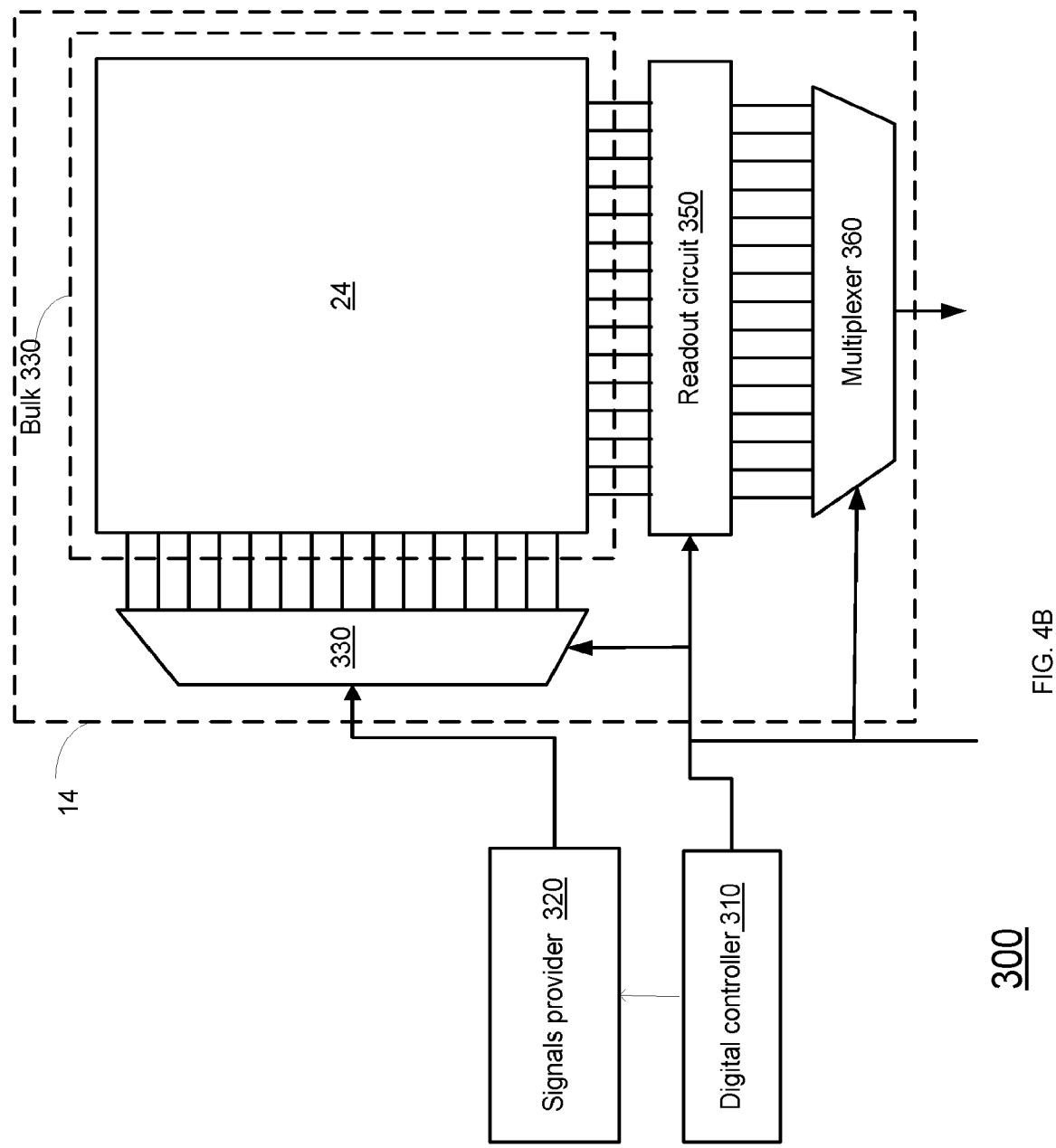
FIG. 4B illustrates a gas sensing device according to an embodiment of the invention.

FIG. 4B illustrates a gas sensing device 300 according to an embodiment of the invention.

In FIG. 4B the interfacing module 380 is illustrates as including (i) a de-multiplexer 330 that is coupled between signals source 320 and array 24, and (ii) a multiplexer 360 that is coupled between readout circuit 350 and an output port of gas sensing device.

Figure 5A:
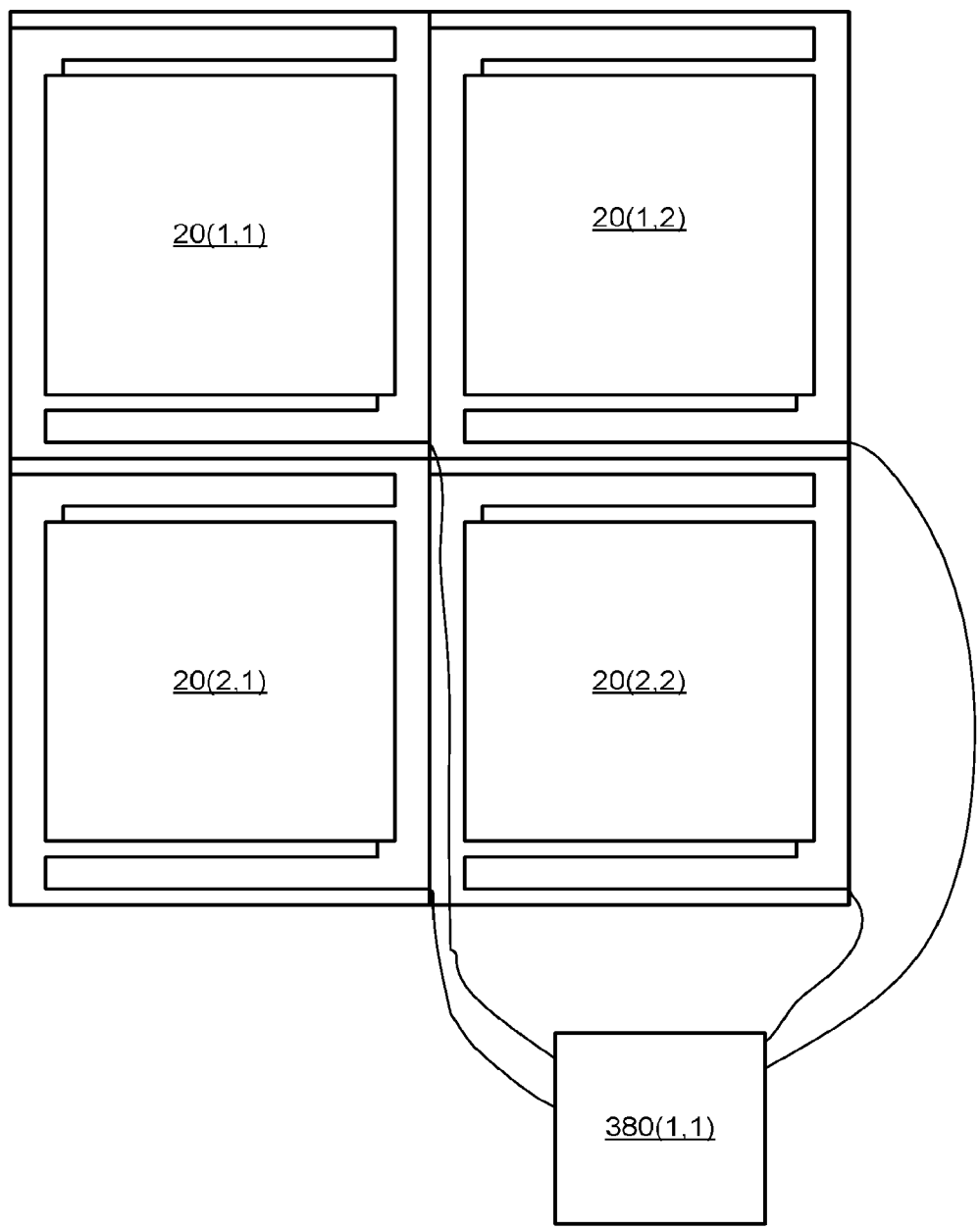
FIG. 5A illustrates gas sensing elements and a part of an interfacing module according to an embodiment of the invention.

FIG. 5A illustrates gas sensing elements 20(1,1), 20(1,2), 20(2,1) and 20(2,2) and a part 380(1,1) of an interfacing module according to an embodiment of the invention.

Part 380(1,1) may provide bias signals to each one of gas sensing elements 20(1,1), 20(1,2), 20(2,1) and 20(2,2) and may receive and/or manipulate detection signals from gas sensing elements 20(1,1), 20(1,2), 20(2,1) and 20(2,2).

For example, part 380(1,1) may perform a manipulation by adding (or averaging) the detection signals from gas sensing elements 20(1,1), 20(1,2), 20(2,1) and 20(2,2).

When each one of gas sensing elements gas sensing elements 20(1,1), 20(1,2), 20(2,1) and 20(2,2) is used to sense a different materials then gas sensing elements 20(1,1), 20(1,2), 20(2,1) and 20(2,2) are capable of detecting a gaseous mixture of up till four different materials.

Each gas sensing element may have a different response to materials—and when exposed to a gaseous mixture of up till four different materials the processing of detection signals of gas sensing elements 20(1,1), 20(1,2), 20(2,1) and 20(2,2) can reveal the composition of the gaseous mixture.

Figure 5B:
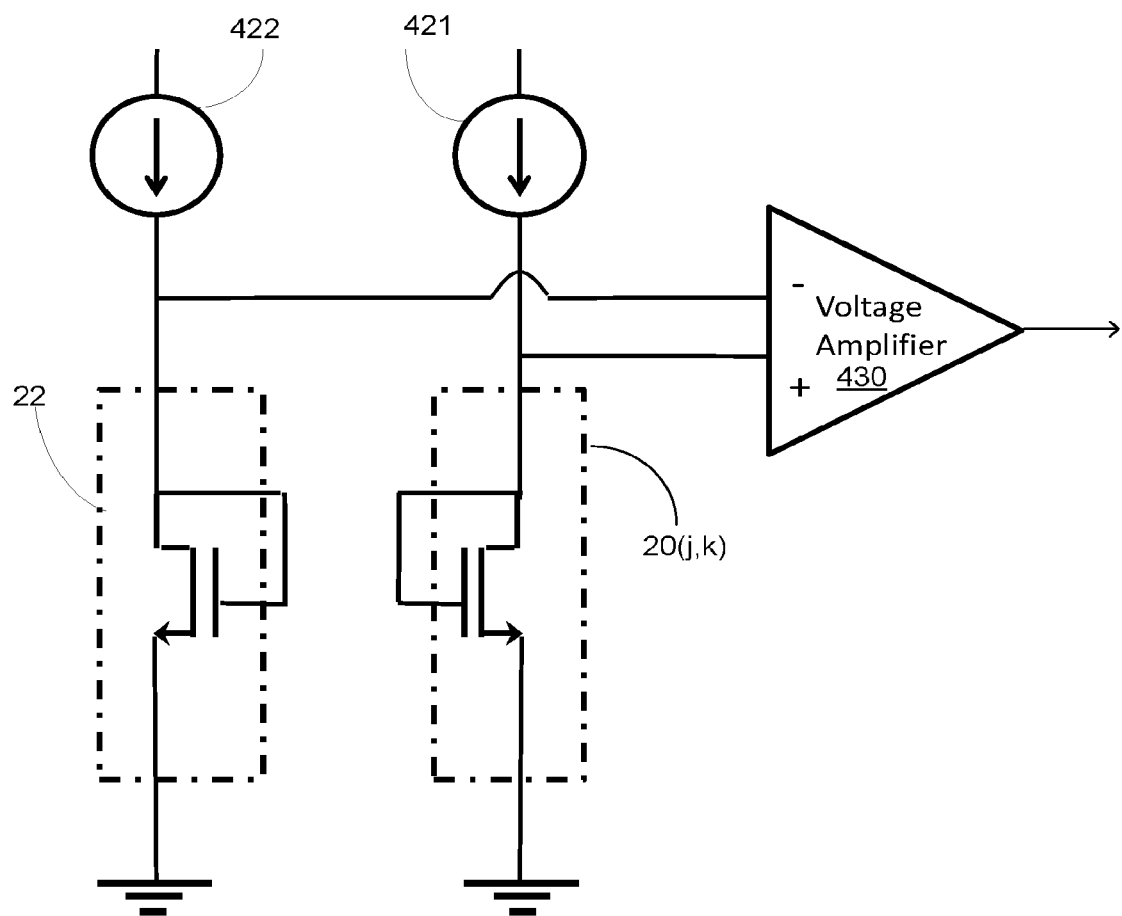
FIG. 5B illustrates a gas sensing element, a reference element, current sources and a voltage amplifier according to an embodiment of the invention.

FIG. 5B illustrates a gas sensing element 20(j,k), a reference element 22, current sources 421 and 422 and a voltage amplifier 430 according to an embodiment of the invention.

Each one of gas sensing element 20(j,k) and reference element 22 has a CMOS transistor that is coupled as a diode but may also be operated with 3 terminals. A detection signal is outputted by gas sensing element 20(j,k) and is a voltage detection signal. The detection signal reflects the gas sensed by the gas sensing element—especially the temperature of the gas reactive element of gas sensing element 20(j,k). A reference signal is a voltage detection signal and reflects the temperature of the CMOS transistor of reference element 22.

The detection signal is fed to a non-inverting input of voltage amplifier 430. The reference signal is fed to an inverting input of voltage amplifier 430. Voltage amplifier 430 calculates the difference between the detection signal and the reference signal.

The reference signal may be provide by any reference source—including a voltage source that does not include a CMOS transistor.

Current sources 421 and 422 may belong to signals source 320 and are provided, via interfacing module 380, to gas sensing element 20(j,k) and reference 22 respectively.

Voltage amplifier 430 may belong to readout circuit 350 of FIGS. 4A and 4B. Voltage amplifier 350 may receive the detection signal via interfacing module 380.

Figure 5C:
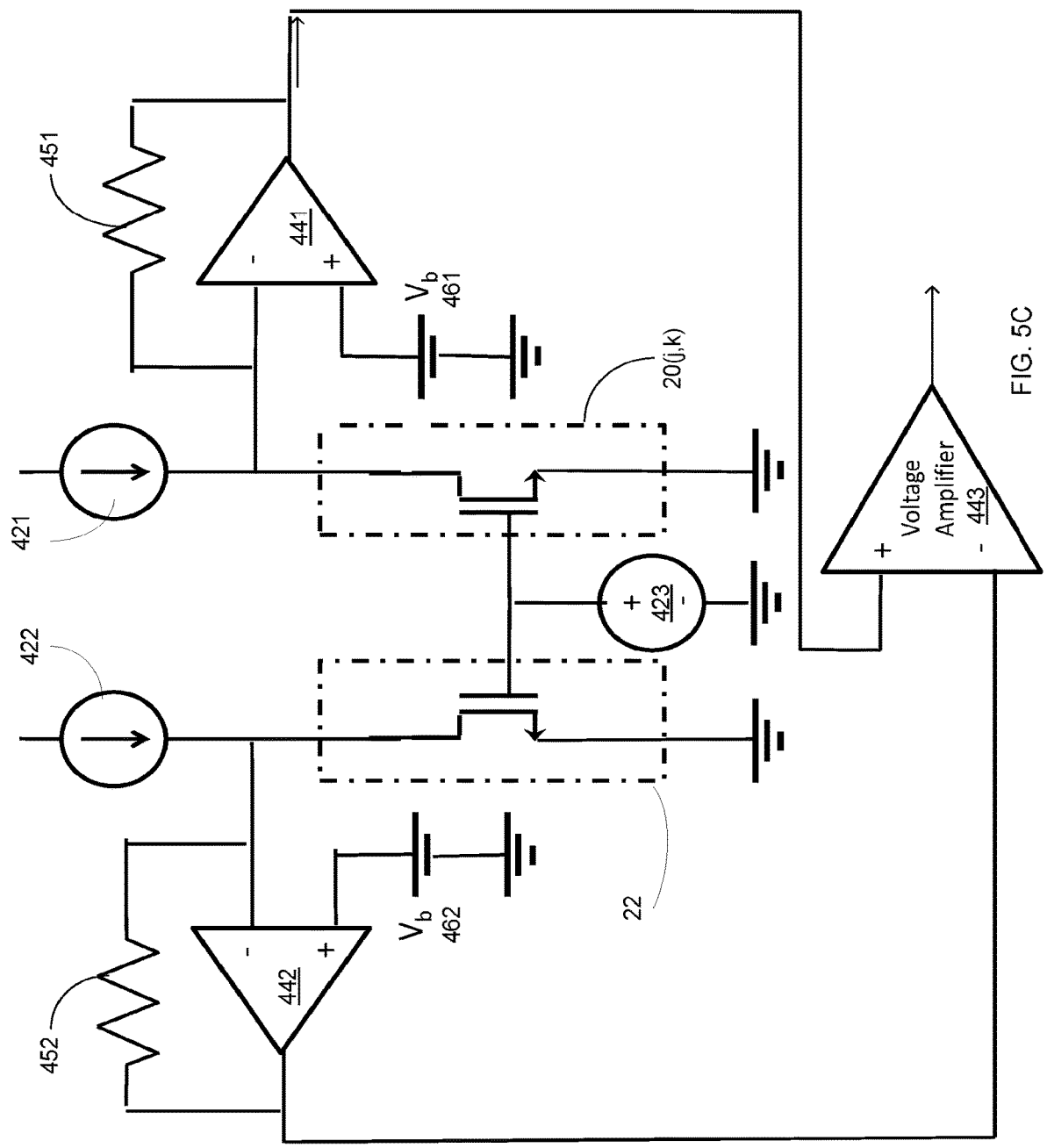
FIG. 5C illustrates a gas sensing element, a reference element, current sources, voltage sources, transimpedance amplifiers, a voltage amplifier and feedback resistors according to an embodiment of the invention.

FIG. 5C illustrates a gas sensing element 20(j,k), a reference element 22, current sources 421 and 422, voltage sources 423, 461 and 462, transimpedance amplifiers 441 and 442, a voltage amplifier 443 and feedback resistors 451 and 452 according to an embodiment of the invention.

In FIG. 5C the detection signal outputted by gas sensing element 20(j,k) is a current detection signal and the reference signal outputted by reference element 22 is a reference current signal.

Voltage source 423 provide a gate bias voltage to the gases of the CMOS transistors of gas sensing element 20(j,k), a reference element 22.

A detection signal is outputted by gas sensing element 20(j,k) and is a current detection signal. The detection signal reflects the gas sensed by the gas sensing element—especially the temperature of the gas reactive element of gas sensing element 20(j,k). A reference signal is a current detection signal and reflects the temperature of the CMOS transistor of reference element 22.

First transimpedance amplifier 441 receives at its non-inverting input a bias voltage from voltage source 461.

A first current that is a difference between a first fixed current (from first current source 421) and the current detection signal is fed to an inverting input of first transimpedance amplifier 441 and to first feedback resistor 451 to provide a first intermediate voltage that is then fed to a non-inverting input of voltage amplifier 443.

A second current that is a difference between a second fixed current (from second current source 422) and the reference current signal is fed to an inverting input of second transimpedance amplifier 442 and to second feedback resistor 452 to provide a second intermediate voltage that is then fed to an inverting input of voltage amplifier 443.

Voltage amplifier 443 outputs an output signal that represents the difference between the reference signal and the detection signal—which indicates the temperature of the gas reactive element of gas sensing element 20(j,k).

FIG. 6 illustrates method 600 according to an embodiment of the invention.

Method 600 may include step 610 of heating, to a predefined temperature, a gas reactive element that belongs to a gas sensing element and has a gas dependent temperature.

Step 610 may be followed by step 620 of generating, by a semiconductor temperature sensing element that belongs to the gas sensing element and is thermally coupled to the gas reactive element, detection signals that are indicative of a temperature of the gas reactive element. The gas sensing element is thermally isolated from a bulk of a gas sensing device.

Step 620 may be followed by step 630 of processing, by a readout circuit of the gas sensing device, the detection signals to provide information about gas that affected the temperature of the gas reactive element.

Method 600 may be executed by any of the gas sensing devices illustrated in any of the drawings.

In the foregoing specification, the invention has been described with reference to specific examples of embodiments of the invention. It will, however, be evident that various modifications and changes may be made therein without departing from the broader spirit and scope of the invention as set forth in the appended claims.

Moreover, the terms "front," "back," "top," "bottom," "over," "under" and the like in the description and in the claims, if any, are used for descriptive purposes and not necessarily for describing permanent relative positions. It is understood that the terms so used are interchangeable under appropriate circumstances such that the embodiments of the invention described herein are, for example, capable of operation in other orientations than those illustrated or otherwise described herein.

The connections as discussed herein may be any type of connection suitable to transfer signals from or to the respective nodes, units or devices, for example via intermediate devices. Accordingly, unless implied or stated otherwise, the connections may for example be direct connections or indirect connections. The connections may be illustrated or described in reference to being a single connection, a plurality of connections, unidirectional connections, or bidirectional connections. However, different embodiments may vary the implementation of the connections. For example, separate unidirectional connections may be used rather than bidirectional connections and vice versa. Also, plurality of connections may be replaced with a single connection that transfers multiple signals serially or in a time multiplexed manner. Likewise, single connections carrying multiple signals may be separated out into various different connections carrying subsets of these signals. Therefore, many options exist for transferring signals.

Although specific conductivity types or polarity of potentials have been described in the examples, it will be appreciated that conductivity types and polarities of potentials may be reversed.

Any arrangement of components to achieve the same functionality is effectively "associated" such that the desired functionality is achieved. Hence, any two components herein combined to achieve a particular functionality may be seen as "associated with" each other such that the desired functionality is achieved, irrespective of architectures or intermedial components. Likewise, any two components so associated can also be viewed as being "operably connected," or "operably coupled," to each other to achieve the desired functionality.

However, other modifications, variations and alternatives are also possible. The specifications and drawings are, accordingly, to be regarded in an illustrative rather than in a restrictive sense.

In the claims, any reference signs placed between parentheses shall not be construed as limiting the claim. The word 'comprising' does not exclude the presence of other elements or steps then those listed in a claim. Furthermore, the terms "a" or "an," as used herein, are defined as one or more than one. Also, the use of introductory phrases such as "at least one" and "one or more" in the claims should not be construed to imply that the introduction of another claim element by the indefinite articles "a" or "an" limits any particular claim containing such introduced claim element to inventions containing only one such element, even when the same claim includes the introductory phrases "one or more" or "at least one" and indefinite articles such as "a" or "an." The same holds true for the use of definite articles. Unless stated otherwise, terms such as "first" and "second" are used to arbitrarily distinguish between the elements such terms describe. Thus, these terms are not necessarily intended to indicate temporal or other prioritization of such elements.

The mere fact that certain measures are recited in mutually different claims does not indicate that a combination of these measures cannot be used to advantage.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

I claim:

1. A gas sensing device, comprising:
a bulk;
an array of gas sensing elements that are thermally isolated from the bulk, wherein each gas sensing element of a plurality of gas sensing elements of the array comprises (i) a gas reactive element that has a gas dependent temperature parameter; (ii) a semiconductor temperature sensing element that is thermally coupled to the gas reactive element and is configured to generate detection signals that are responsive to a temperature of the gas reactive element; and (iii) multiple heating elements that are configured to heat the gas reactive element to at least one predefined temperature;
a signals source; and an interfacing module;
wherein the interfacing module electrically couples the array to the signals source;
wherein the signals source is configured to (a) supply bias signals for setting working points of semiconductor temperature sensing elements of the plurality of gas sensing elements; and (b) supply other bias signals for determining a heating of multiple heating elements of the plurality of gas sensing elements.

2. The gas sensing device according to claim 1, further comprises at least one reference sensing element that comprises a semiconductor temperature sensing element that is not thermally coupled to a gas reactive element.

3. The gas sensing device according to claim 1, wherein at least two gas sensing elements of the array are configured to sense different gases.

4. The gas sensing device according to claim 1, wherein at least two gas sensing elements of the array differ from each other by their gas reactive elements.

5. The gas sensing device according to claim 1, wherein at least two gas sensing elements of the array have a same gas reactive element.

6. The gas sensing device according to claim 1 wherein in each gas sensing element of the plurality of gas sensing elements the multiple heating elements are fed by different conductors.

7. The gas sensing device according to claim 6, wherein in each gas sensing element of the plurality of gas sensing elements the multiple heating elements are positioned on different sides of the semiconductor temperature sensing element without completely surrounding the semiconductor temperature sensing element.

8. The gas sensing device according to claim 6, wherein in each gas sensing element of the plurality of gas sensing elements the multiple heating elements are spaced apart from the semiconductor temperature sensing element.

9. The gas sensing device according to claim 6, wherein in each gas sensing element of the plurality of gas sensing elements the multiple heating elements are polysilicon resistors that are spaced apart from the semiconductor temperature sensing element.

10. The gas sensing device according to claim 6, wherein the at least one predefined temperature comprises multiple predefined temperatures that are associated with a sensing of multiple gases that differ from each other; wherein in each gas sensing element of the plurality of gas sensing elements the multiple heating elements are configured to heat the gas reactive element, at different points in time, to the multiple predefined temperatures.

11. The gas sensing device according to claim 6 wherein each heating element is configured to heat the gas reactive element in a non-continuous manner.

12. The gas sensing device according to claim 1, further comprising a readout circuit; wherein the interfacing module also electrically couples the array to the readout circuit; wherein the readout circuit is configured to read detection signals from the some gas sensing elements of the array.

13. The gas sensing device according to claim 12 wherein the signals source is configured to send a bias signal that is a first pulse for setting a working point of a semiconductor temperature sensing element of a gas sensing element of the plurality of gas sensing elements and to send an other bias signal that is a second pulse for determining heating of multiple heating elements of the gas sensing element y.

14. The gas sensing device according to claim 13 wherein the signals source is configured to output the first pulse and the second pulse simultaneously.

15. The gas sensing device according to 13 wherein the signals source is configured to output the second pulse before outputting the first pulse.

16. The gas sensing device according to claim 1 wherein the signals source is configured to provide the bias signals and the other bias signals in a continuous manner.

17. The gas sensing device according to claim 1 wherein the signals source is configured to provide the bias signals and the other bias signals in a noncontinuous manner.

18. The gas sensing device according to claim 1 wherein each gas sensing element of the plurality of gas sensing elements is mechanically supported by at least one supporting element.

19. The gas sensing device according to claim 1 wherein each gas sensing element of the plurality of gas sensing elements is mechanically supported by a plurality of spaced apart supporting elements.

20. The gas sensing device according to claim 1 wherein the bulk is micro-machined or nano-machined to form a gap between the bulk and the array of gas sensing elements.

21. The gas sensing device according to claim 1, wherein in each gas sensing element of the plurality of gas sensing elements the semiconductor temperature sensing element is a Complementary Metal Oxide Semiconductor (CMOS) temperature sensor.

22. The gas sensing device according to claim 1 wherein the array comprises a plurality (N) of gas sensing elements that are configured, at a certain point in time, to differ from each other by their response to materials; wherein the gas sensing device is configured to detect a composition of up to N different gaseous materials by processing the detection signals from the plurality of gas sensing elements.

23. The gas sensing device according to claim 1 wherein in each gas sensing element of the plurality of gas sensing elements the semiconductor temperature sensing elements are coupled to multiple semiconductor temperature sensing element (TSE) conductors that exhibit a pool thermal conductivity.

24. The gas sensing device according to claim 1 wherein in each gas sensing element of the plurality of gas sensing elements the semiconductor temperature sensing element is coupled to multiple semiconductor temperature sensing element (TSE) conductors that are made of doped polysilicon or active silicon.

\* \* \* \* \*